US011344075B2

(12) United States Patent
Greenblatt et al.

(10) Patent No.: US 11,344,075 B2
(45) Date of Patent: May 31, 2022

(54) SMART PREDICTION OF NEUROLOGICAL INJURY

(71) Applicant: INTERNATIONAL BUSINESS MACHINES CORPORATION, Armonk, NY (US)

(72) Inventors: Michael L. Greenblatt, Jefferson Hills, PA (US); Heidi Lagares-Greenblatt, Jefferson Hills, PA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 883 days.

(21) Appl. No.: 16/176,745

(22) Filed: Oct. 31, 2018

(65) Prior Publication Data

US 2020/0128899 A1 Apr. 30, 2020

(51) Int. Cl.
*G01N 33/48* (2006.01)
*A42B 3/04* (2006.01)
(Continued)

(52) U.S. Cl.
CPC ............ *A42B 3/046* (2013.01); *A61B 5/6803* (2013.01); *A61B 5/6814* (2013.01); *A61B 5/4064* (2013.01);
(Continued)

(58) Field of Classification Search
CPC ..... A42B 3/046; A61B 5/6803; A61B 5/6814; A61B 5/4064; A61B 5/4076;
(Continued)

(56) References Cited

U.S. PATENT DOCUMENTS 10,154,460 B1 * 12/2018 Miller .................. A61B 5/742
10,431,343 B2 * 10/2019 Pauws .................. G16B 40/00
(Continued)

OTHER PUBLICATIONS

Abigail Tracy, "Could This Helmet Save Football From The Sport's Concussion Problem?," Forbes, https://www.forbes.com/sites/abigailtracy/2016/02/04/nfl-cte-football-concussions-injuries-helmet-vicis-zero1-super-bowl/#70adf8c75f05, Feb. 2016, 8 pages.
(Continued)

*Primary Examiner* — Anh V La
(74) *Attorney, Agent, or Firm* — Cantor Colburn LLP (57) ABSTRACT

Systems, methods, and computer-readable media are described for predicting a neurological injury to a participant in an activity. The activity can be, for example, an athletic activity that involves repeated, high-impact collisions between participants. Sensor data reflecting interactions between participants in the activity is received from various wearable and non-wearable sensors. The sensor data is evaluated in conjunction with a baseline neurological risk profile of a participant to determine a likelihood that the participant has suffered a potential neurological injury. If this likelihood meets a threshold risk level, an onsite request/response test is initiated to glean more information relating to the participant's condition. Response data associated with the onsite test is cognitively evaluated to determine an updated likelihood of neurological injury to the participant and a follow-up action is determined based on the updated likelihood of neurological injury.

20 Claims, 5 Drawing Sheets

(51) Int. Cl.
*A61B 5/00* (2006.01)
*A63B 71/10* (2006.01)
*G01L 5/00* (2006.01)

(52) U.S. Cl.
CPC .......... *A61B 5/4076* (2013.01); *A61B 5/6898* (2013.01); *A61B 5/742* (2013.01); *A61B 2503/10* (2013.01); *A61B 2560/0462* (2013.01); *A61B 2562/0219* (2013.01); *A63B 71/10* (2013.01); *A63B 2220/806* (2013.01); *A63B 2225/20* (2013.01); *G01L 5/0052* (2013.01)

(58) Field of Classification Search
CPC ... A61B 5/6898; A61B 5/742; A61B 2503/10; A61B 2560/0462; A61B 2562/0219; A61B 5/7275; A63B 71/10; A63B 2220/806; A63B 2225/20; G01L 5/0052; G16H 20/70; G16H 40/63; G16H 50/20; G16H 50/30
USPC ........... 340/573.1, 539.12; 702/19, 179, 180, 702/183, 187; 600/301, 509, 515
See application file for complete search history.

(56) References Cited

U.S. PATENT DOCUMENTS

| | | | |
|---|---|---|---|
| 2008/0162352 A1* | 7/2008 | Gizewski | G16H 50/20 705/50 |
| 2013/0150684 A1 | 6/2013 | Cooner | |
| 2013/0167290 A1 | 7/2013 | Ben Ezra | |
| 2014/0039354 A1 | 2/2014 | Greenwald et al. | |
| 2015/0040685 A1 | 2/2015 | Nicholson et al. | |
| 2018/0333065 A1* | 11/2018 | Troup | A61B 5/4064 |

OTHER PUBLICATIONS

Daniel Roberts, "Here's How the NFL Might Combat Concussions," Fortune, http://fortune.com/2015/12/31/nfl-concussion-technology, Dec. 2015, 5 pages.

Dipo Faloyin, "NFL Invests $20M in Concussion Prevention," Newsweek Sports, http://www.newsweek.com/nfl-invest-20m-concussion-prevention-402559, Dec. 2015, 3 pages.

Matthew Rocco, "NFL, Under Armour and GE Invest in Concussion-Fighting Technology," FOX Business, https://www.foxbusiness.com/features/nfl-under-armour-and-ge-invest-in-concussion-fighting-technology, Dec. 2015, 3 pages.

Mike Vorkunov, "New technology is next wave of scouting and analysis in NFL, if league allows it," NJ Advance Media for NJ.com, http://www.nj.com/giants/index.ssf/2013/05/new_technology_struggling_to_m.html, May 2013, 11 pages.

Sean Wagner-McGough, "New NFL rule gives concussion spotters power to stop games," CBSSPORTS.com, http://www.cbssports.com/nfl/news/new-nfl-rule-gives-concussion-spotters-power-to-stop-games, Aug. 2015, 2 pages.

* cited by examiner

SMART PREDICTION OF NEUROLOGICAL INJURY

BACKGROUND

The present invention relates generally to predicting neurological injury to an individual, and more particularly, to predicting neurological injury to a participant in an activity that involves physical contact.

A number of human activities involve repeated physical contact between participants. In particular, certain athletic activities, such as American football or rugby, involve repeated physical high-impact collisions between participants. Such repeated collisions often involve significant amounts of force and can lead to various physical injuries to participants. Perhaps most concerning among these are injuries affecting the head, neck, or spine.

In recent years, certain sports have been subjected to increased scrutiny for the potential long-term risks and complications associated with repeated neurological injury to participants. For instance, the National Football League (NFL) has received intense scrutiny in recent years over the possible link between repeated head trauma (e.g., concussions) that players sustain during their playing careers and a degenerative brain disease known as chronic traumatic encephalopathy (CTE). The NFL has responded to this scrutiny in various ways including by changing rules and regulations in an attempt to minimize the risk of neurological injury to athletes; developing a concussion protocol that requires independent medical professionals evaluate athletes to determine whether they should be allowed to continue playing or must undergo further evaluation; ensuring that players complete a recovery process if diagnosed with a concussion before being allowed to play again; introducing impact-absorbing technology into equipment worn by athletes; and so forth. Existing approaches, however, for reducing the likelihood of neurological injury to a participant in an activity involving repeated high-impact physical contact such as those adopted by the NFL suffer from a number of drawbacks, technical solutions to which are described herein.

SUMMARY

In one or more example embodiments, a method for predicting a neurological injury to a particular participant in an activity is disclosed. The method includes receiving sensor data relating to interactions between multiple participants in the activity, where the multiple participants include the particular participant. The method further includes determining a baseline neurological injury risk profile for the particular participant and performing, based at least in part on the sensor data and the baseline neurological injury risk profile, a cognitive risk analysis to determine a likelihood of the neurological injury to the particular participant. The method additionally includes determining that the likelihood of the neurological injury to the particular participant is at least as large as a threshold risk level and initiating an onsite test for the neurological injury to the particular participant.

In one or more other example embodiments, a system for predicting a neurological injury to a particular participant in an activity is disclosed. The system includes at least one memory storing computer-executable instructions and at least one processor configured to access the at least one memory and execute the computer-executable instructions to perform a set of operations. The operations include receiving sensor data relating to interactions between multiple participants in the activity, where the multiple participants include the particular participant. The operations further include determining a baseline neurological injury risk profile for the particular participant and performing, based at least in part on the sensor data and the baseline neurological injury risk profile, a cognitive risk analysis to determine a likelihood of the neurological injury to the particular participant. The operations additionally include determining that the likelihood of the neurological injury to the particular participant is at least as large as a threshold risk level and initiating an onsite test for the neurological injury to the particular participant.

In one or more other example embodiments, a computer program product for predicting a neurological injury to a particular participant in an activity is disclosed. The computer program product includes a non-transitory storage medium readable by a processing circuit, the storage medium storing instructions executable by the processing circuit to cause a method to be performed. The method includes receiving sensor data relating to interactions between multiple participants in the activity, where the multiple participants include the particular participant. The method further includes determining a baseline neurological injury risk profile for the particular participant and performing, based at least in part on the sensor data and the baseline neurological injury risk profile, a cognitive risk analysis to determine a likelihood of the neurological injury to the particular participant. The method additionally includes determining that the likelihood of the neurological injury to the particular participant is at least as large as a threshold risk level and initiating an onsite test for the neurological injury to the particular participant.

BRIEF DESCRIPTION OF THE DRAWINGS

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. In the drawings, the left-most digit(s) of a reference numeral identifies the drawing in which the reference numeral first appears. The use of the same reference numerals indicates similar, but not necessarily the same or identical components. However, different reference numerals may be used to identify similar components as well. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION

Example embodiments relate to, among other things, systems, methods, computer-readable media, techniques, and methodologies for predicting a neurological injury to a participant in an activity. In example embodiments, the activity may include any activity in which physical contact occurs repeatedly between participants due to the nature of the activity. For instance, the activity may be an athletic activity such as American football, rugby, boxing, mixed martial arts, or the like in which repeated, high-impact collisions occur between athletes, often involving significant amounts of force. As another non-limiting example, the activity may be a non-athletic activity such as a "mosh pit" at a concert in which participants in the mosh pit intentionally collide with one another. It should be appreciated that the above examples of activities involving physical contact between participants that runs the risk of neurological injury are merely illustrative and not exhaustive. In example embodiments, a neurological injury may include any injury to the head, neck, or spine including, without limitation, a concussion, a brain hemorrhage, a spinal injury that may lead to temporary or permanent paralysis, or the like. While example embodiments are described herein with respect to predicting neurological injury, it should be appreciated that such embodiments are also applicable to other types of physical injuries. In addition, while example embodiments of the invention represent a technical improvement over conventional injury detection techniques, such example embodiments can also be used in conjunction with one or more existing concussion diagnostic techniques to supplement and/or enhance such techniques.

Illustrative methods in accordance with example embodiments of the invention and corresponding data structures (e.g., program modules) for performing the methods will now be described. It should be noted that each operation of the method 200 and/or the method 300 may be performed by one or more of the program modules or the like depicted in FIG. 1 or FIG. 4, whose operation will be described in more detail hereinafter. These program modules may be implemented in any combination of hardware, software, and/or firmware. In certain example embodiments, one or more of these program modules may be implemented, at least in part, as software and/or firmware modules that include computer-executable instructions that when executed by a processing circuit cause one or more operations to be performed. A system or device described herein as being configured to implement example embodiments may include one or more processing circuits, each of which may include one or more processing units or nodes. Computer-executable instructions may include computer-executable program code that when executed by a processing unit may cause input data contained in or referenced by the computer-executable program code to be accessed and processed to yield output data.

Figure 1:
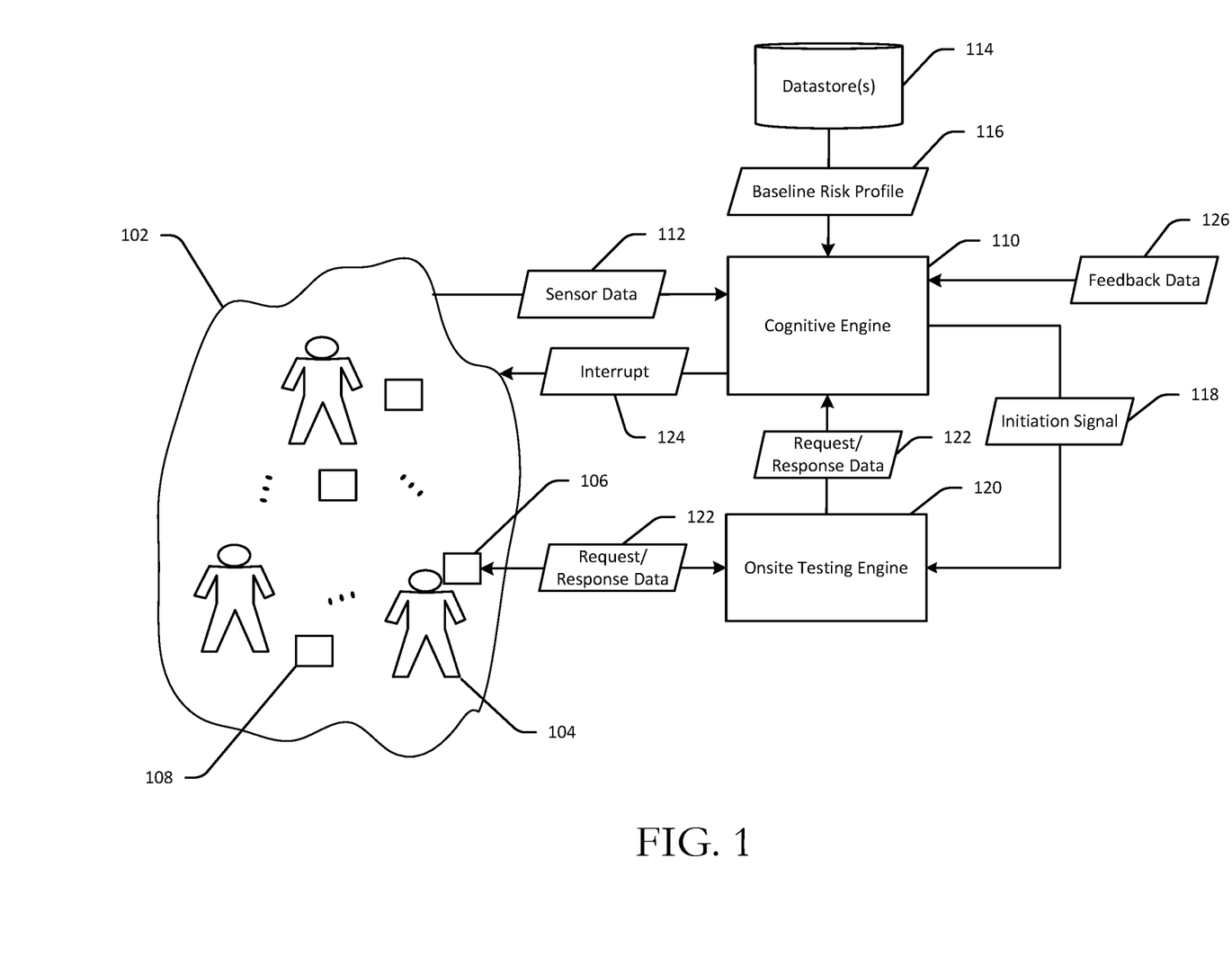
FIG. 1 is a schematic hybrid data flow/block diagram illustrating smart prediction of neurological injury in accordance with one or more example embodiments.
Figure 2A:
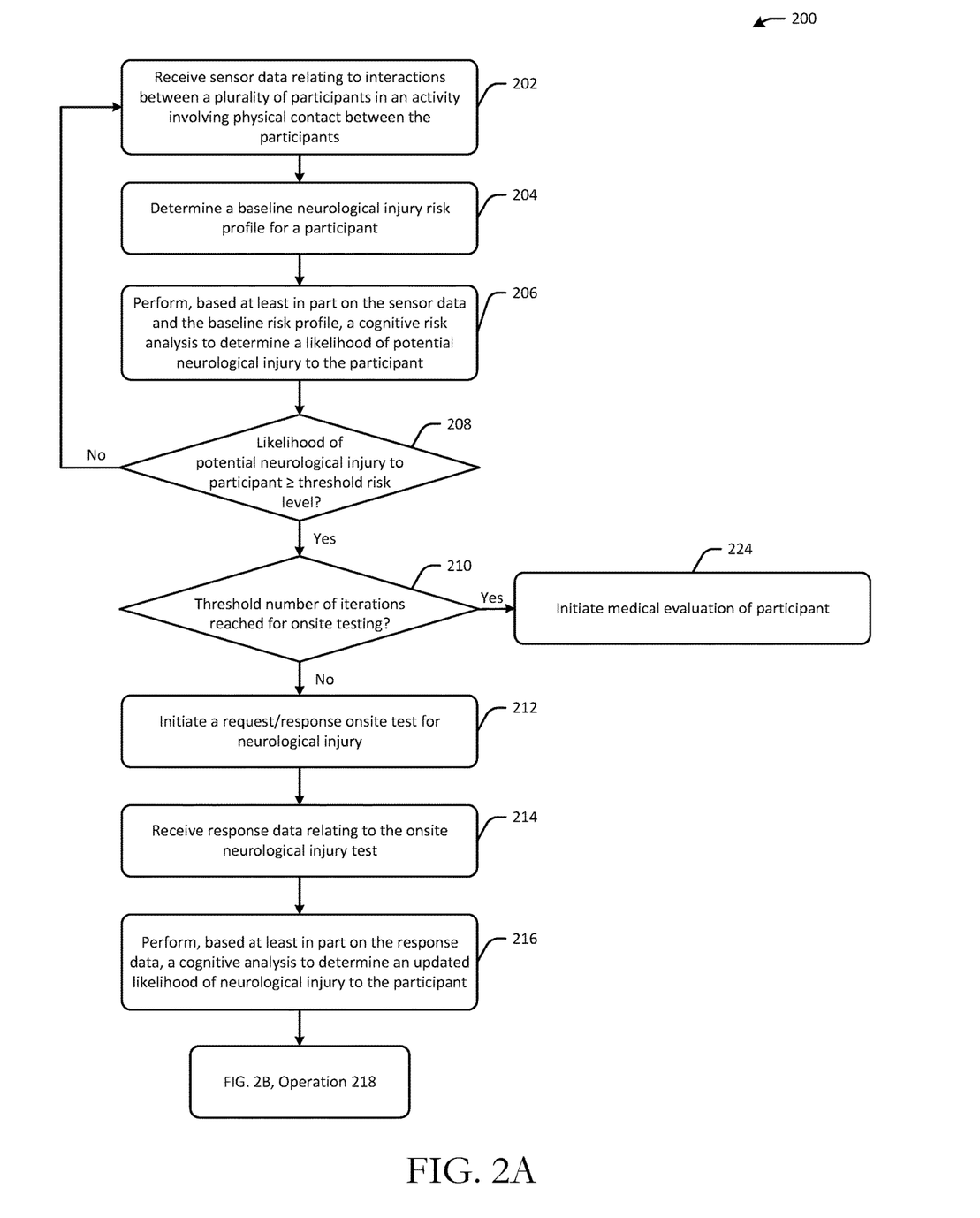
FIGS. 2A and 2B are process flow diagrams of an illustrative method for predicting a neurological injury to a participant in an activity in accordance with one or more example embodiments.
Figure 2B:
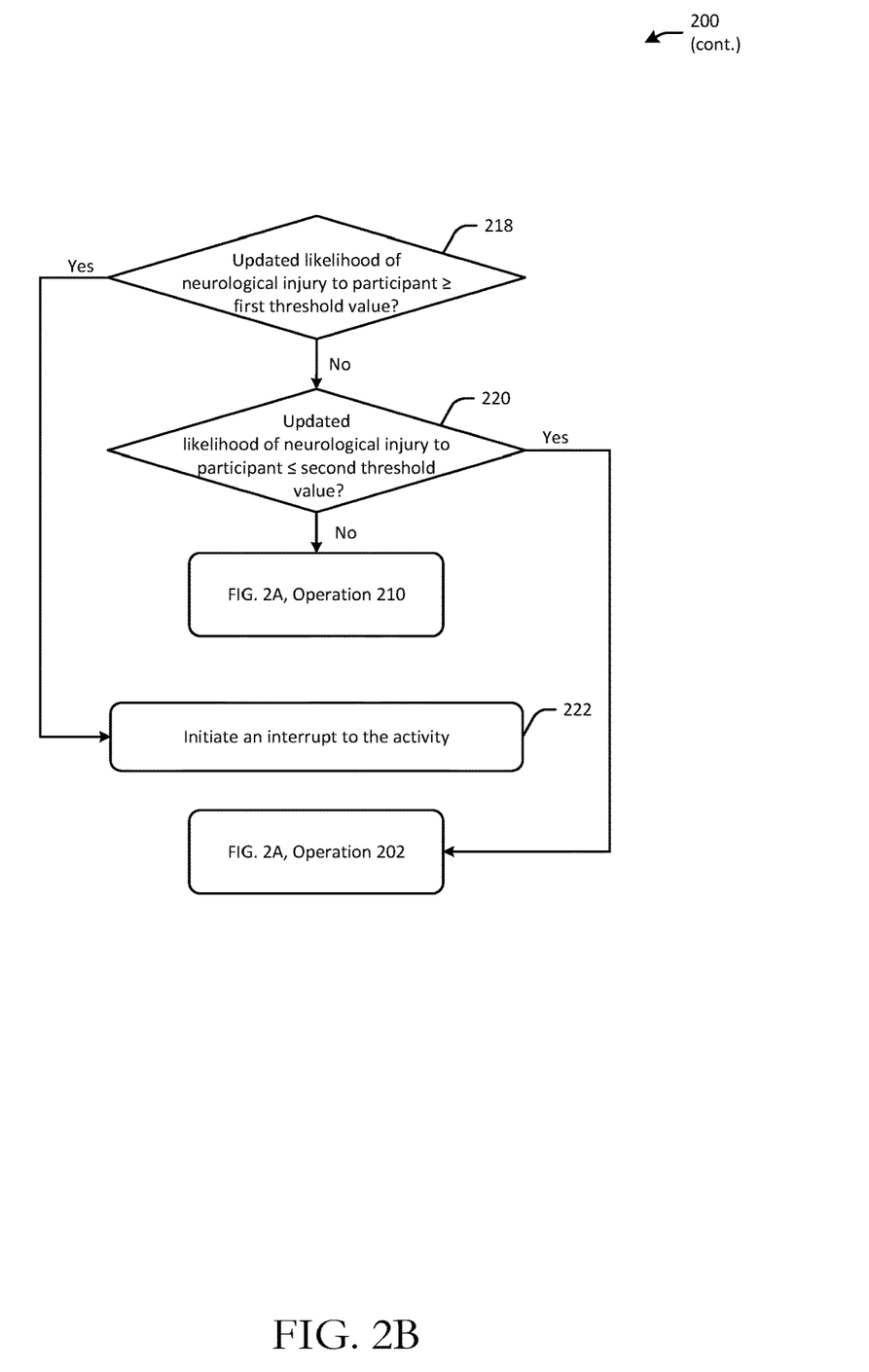

FIG. 1 is a schematic hybrid data flow/block diagram illustrating smart prediction of neurological injury in accordance with one or more example embodiments. FIGS. 2A and 2B are process flow diagrams of an illustrative method 200 for predicting a neurological injury to a participant in an activity in accordance with one or more example embodiments. Each of FIGS. 2A and 2B will be described in conjunction with FIG. 1 hereinafter.

Referring first to FIG. 1, an environment 102 is depicted in which an activity involving multiple participants is occurring. In example embodiments, the activity is an athletic activity such as a sporting contest that by its nature involves repeated physical contact between participants, where such contact often includes high-impact collisions with significant amounts of force. In those example embodiments in which the activity is a sporting activity, the environment 102 may be a field, arena, stadium, or any other venue in which such an activity may take place. For ease of explanation, example embodiments of the invention will be described hereinafter with respect the example activity of an American football game.

Various sensors may be present within the environment 102. The sensors may capture various types of sensor data relating to interactions between the participants during the activity. In example embodiments, the sensors may include wearable sensors 106 that may be integrated or otherwise disposed on equipment of a player such as a player's helmet. A wearable sensor may capture force data, acceleration data, or the like over time for a player. As will be described in more detail later in this disclosure, the wearable sensor data can be assessed to determine, among other things, interaction patterns between players such as, for example, the number/degree of high-impact collisions involving a player; portions of a game that involve a greater frequency of high-impact collisions; particular player positions that are more susceptible to high-impact collisions; or the like. As used herein, the term "high-impact collision" can refer to any physical contact between participants in an activity that involve applied forces exceeding a threshold value, perhaps over some threshold period of time and/or with a threshold frequency of occurrence.

In example embodiments, the sensors also include sensors 108 disposed within the environment 102 but which are not integrated with or otherwise disposed on players' equipment. Such sensors may include, for example, image sensors to capture still images and/or video of player interactions on the field. The sensors 108 in the environment 102 may also include microphones to capture audio of player interactions on the field. In example embodiments, the sensors 108 further include vibration sensors, accelerometers, Global Positioning System (GPS) receivers, or the like to capture additional forms of sensor data relating to player interactions.

Referring now to FIG. 2A in conjunction with FIG. 1, in example embodiments, a cognitive engine 110 receives sensor data 112 from the various sensors in the environment 102 including wearable sensors 106 disposed on players' helmets, pads, uniforms, or the like as well as non-wearable sensors 108 disposed in the environment 102. The cognitive engine 110 may receive the sensor data 112 at periodic intervals; as part of a continuous data stream; and/or in response to a trigger (e.g., acceleration/force data that exceeds some threshold). Receiving the sensor data 112 as a continuous data stream may, for example, allow the cognitive engine to identify patterns and changes in conditions relating to the movements and interactions of the players. For instance, in example embodiments, for any given player, the cognitive engine may identify various activity patterns for a player including, without limitation, the percentage of time a player spends stationary or at a low speed; the percentage of time the player is accelerating; the number/frequency of high-impact collisions that a player is involved in; the average amount of time that a player spends on the ground after a collision; and so forth.

At block 204 of the method 200, in example embodiments, the cognitive engine 110 accesses a baseline neurological risk profile 116 for a player 104. The baseline profile may be stored in one or more datastores 114. In example embodiments, a respective baseline profile may be maintained in the datastore(s) 114 for each player. The baseline profile 116 may include historical data relating to the player's 104 previous interactions with other players during prior games including, without limitation, historical sensor data captured during the prior games; data relating to prior cognitive analyses performed on the historical sensor data (e.g., activity patterns gleaned for the player 104); and so forth. In example embodiments, the baseline profile 116 for the player 104 also includes historical sensor data and/or patterns identified therefrom for one or more other players. Further, in example embodiments, the baseline profile 116 includes data identifying characteristics of the sport the player 104 competes in (e.g., the number/type of equipment the players wear, the relative frequency of high-impact collisions that occur in the sport as compared to other sports, etc.). In example embodiments, the cognitive engine 110 may also access baseline profiles associated with one or more players other than the player 104.

At block 206 of the method 200, in example embodiments, the cognitive engine 110 performs a cognitive analysis based at least in part on the received sensor data 112 and the baseline risk profile 116 to determine a likelihood that a player of interest has suffered a potential neurological injury such as a concussion. The cognitive engine 110 may, for example, evaluate force and acceleration data received among the sensor data 112 to determine whether a player of interest has been involved in a high-impact collision. In example embodiments, the cognitive engine 110 evaluates the sensor data 112 (e.g., vibrational sensor data) to determine if there are any irregularities in the player's movement such as whether the player is walking slower than expected for that player; whether the player is more unstable (e.g., wobbly) than expected for that player; whether the player is remaining stationary on the field for a longer than expected time after a collision; and so forth. In example embodiments, to determine whether there are irregularities in the player's movement, the cognitive engine 110 compares the sensor data 112 to data contained in the baseline risk profile 116 which indicates normal/expected player movements for the player of interest.

Further, in example embodiments, the cognitive engine 110 takes into account various information contained in the baseline risk profile 116 for the player of interest and/or baseline risk profile(s) for one or more other players to determine the likelihood of potential neurological injury to the player of interest. Such information may include, without limitation, the player of interest's position; the position of another player involved in the high-impact collision with the player of interest; the relative difference in weight between the player of interest and another player involved in the high-impact collision; whether the player of interest initiated the contact (e.g., the tackler or the one tackled); the tendency of the particular player of interest to be involved in high-impact collisions and/or the tendency for a player at the position played by the player of interest to be involved in high-impact collisions; and so forth. In example embodiments, the cognitive engine 110 takes into account the various information contained in the baseline risk profile 116 and/or in one or more other baseline risk profiles to weight or otherwise refine the assessment of sensor data 112 that may be indicative of a high-impact collision.

In certain example embodiments, the cognitive engine 110 is a machine learning construct such as a type of neural network (e.g., a convolutional neural network) that is capable of being trained based on ground-truth data to more accurately determine the likelihood that a player has sustained a neurological injury. The ground-truth data may include, for example, image data, video data, and/or other forms of sensor data (e.g., force/acceleration data) known to be associated with the occurrence of neurological injury. The cognitive engine 110 may be trained to learn patterns from such historical ground-truth data using, for example, a computer vision-based approach.

For example, the cognitive engine 110 may learn the types of collisions that have resulted in neurological injury in the past such as collisions that involve players between whom there is a significant (e.g., above a threshold value) deviation in weight or height; collisions that produce force/acceleration data that exceeds a threshold value; collisions that involve particular player positions or particular types of plays (e.g., a safety in American football tackling a receiver coming over the middle of the field); and so forth. Further, in certain example embodiments, ground-truth data including video data, image data, inertial sensor data, or the like relating to player interactions that were ultimately determined to have resulted in neurological injury but which were not detected on the field can also be input to the cognitive engine 110. The cognitive engine 110 can attempt to learn patterns from this data that can be used to avoid failing to detect subsequent incidents of neurological injury in similar situational circumstances.

In example embodiments, the cognitive engine 110 performs the cognitive risk analysis at block 206 in real-time such that a determination can be made dynamically as to whether to initiate an onsite test for potential neurological injury to a player. More specifically, at block 208 of the method 200, in example embodiments, the cognitive engine 110 determines whether the likelihood of potential neurological injury to the player of interest determined based on the cognitive analysis performed at block 206 satisfies a threshold risk level. As used herein, and depending on the implementation, a first value satisfies a second value (e.g., a threshold value) if the first value is strictly greater than the second value; greater than or equal to the second value; strictly less than the second value; or less than or equal to the second value.

In response to a negative determination at block 208 indicating that the likelihood of potential neurological injury to the player of interest does not meet the threshold risk level, the method 200 returns to block 202 where additional sensor data 112 is received and the cognitive analysis is again performed on this additional sensor data 112. In this manner, in example embodiments, player interactions are continually monitored and sensor data relating thereto is captured and cognitively analyzed on a continual basis throughout a sporting event until a determination is made that the likelihood of potential neurological injury to a player meets the threshold amount of risk for initiating the onsite testing. It should be appreciated that the cognitive analysis performed at block 206 can be performed with respect to different players at different iterations of the method (e.g., can be performed with respect to a first player involved in a collision and a second different player involved in a later collision) and/or can be performed in parallel for multiple players at any given iteration of the method 200.

In response to a positive determination at block 208, the cognitive engine 110 may send an initiation signal 118 to an onsite testing engine 120 to initiate, at block 212 of the method 200, an onsite test to attempt to determine with more certainty whether a player of interest has suffered a neurological injury. In example embodiments, the onsite test may be request/response protocol designed to glean more information as to whether a player has suffered a neurological injury. In certain example embodiments, prior to initiating the onsite testing, the cognitive engine 110 (or the onsite testing engine 120) determines whether a threshold number of iterations has been reached for the onsite testing. In example embodiments, the onsite testing engine 120 only proceeds with the onsite testing if the threshold number of iterations has not been reached.

In example embodiments, the onsite testing engine 120 may reside remotely from the environment 102 in which the onsite testing is performed and may be configured to communicate with various onsite devices. For instance, the onsite testing engine 120 may be configured to communicate with and/or receive data from onsite devices such as speakers, sensors, microphones, still image cameras, video cameras, wearable devices, ubiquitous devices, devices activated dynamically on command, or the like in connection with the onsite testing. These onsite devices may be integrated with cameras; player uniforms or other equipment (e.g., helmets, pads, shoes, etc.); objects used by players to play the sport (e.g., a bat, a ball, etc.); stationary objects present in the environment (e.g., a goalpost); or the like. In example embodiments, as part of the onsite testing, the onsite testing engine 120 presents a series of questions or requests to a player via an onsite device (e.g., a speaker integrated with the player's helmet or other equipment). Various other onsite devices (e.g., a microphone, a video camera, a still image camera, etc.) capture the player's responses to the questions/requests and relay this data to the onsite testing engine 120.

In example embodiments, the questions/requests posed to the player and/or the player's responses thereto constitute request/response data 122 that is exchanged between the onsite testing engine 120 and the onsite devices and which the onsite testing engine 120 sends to the cognitive engine 110. At block 216 of the method 200, in example embodiments, the cognitive engine 110 performs a cognitive analysis based at least in part on the request/response data 122 to determine an updated likelihood of neurological injury to the player of interest. In example embodiments, the cognitive analysis performed at block 216 may include comparing the request/response data 122 to baseline data indicative of expected player responses to the series of questions/requests presented during the onsite testing. In example embodiments, the player's responses to the series of questions/requests presented to the player as part of the onsite testing may serve to further inform the prior cognitive analysis performed by the cognitive engine 110 at block 206 in order to obtain, at block 216, a more accurate assessment of the likelihood of neurological injury to the player.

Referring now to FIG. 2B, at block 218 of the method 200, in example embodiments, the cognitive engine 110 determines whether the updated likelihood of neurological injury to the player of interest satisfies (e.g., is greater than or equal to) a first threshold value. The first threshold value may be a value indicative of greater certainty that the player has suffered a neurological injury. As such, in response to a positive determination at block 218, the cognitive engine 110 may initiate an interrupt 124 at block 222 of the method 200 to allow for more comprehensive neurological testing to be performed on the player. In example embodiments, the interrupt 124 may be a signal or notification (e.g., a light, a message, a speaker announcement, a highlight shown on video monitors in the environment 102, etc.) that is potentially sent to an onsite device to inform a coach, manager, medical professional, or the like to remove the player from the environment 102 (e.g., a playing field) in order to perform a more comprehensive evaluation of the player for potential neurological injury. For instance, the onsite testing that is initially performed on the player to determine the updated likelihood of neurological injury to the player may be an initial phase of a concussion protocol, while the more comprehensive evaluation performed after the interrupt 124 is issued may be a later, more detailed phase of the concussion protocol. In example embodiments, after the interrupt 124 is issued, the activity may be temporarily halted (e.g., a timeout taken) to allow the player to leave or be removed from the field for evaluation on the sideline.

On the other hand, in response to a negative determination at block 218, the cognitive engine 110 may determine, at block 220 of the method 200, whether the updated likelihood of potential neurological injury to the player of interest satisfies (e.g., is less than or equal to) a second threshold value. In example embodiments, a positive determination at block 220 indicates that the likelihood of neurological injury to the player is low based on the cognitive analysis of the request/response data 122, and as such, the method 200 may again proceed from block 202, where the monitoring of player interactions continues and additional sensor data 112 relating thereto is provided to the cognitive engine 110.

On the other hand, a negative determination at block 220 occurs when the updated likelihood of neurological injury to the player of interest falls between the first threshold value and the second threshold value, thereby indicating a degree of uncertainty as to whether the player has truly suffered a neurological injury. In such example scenarios, the onsite testing may be repeated to attempt to gather more information to refine the determination of the likelihood of neurological injury. Thus, in response to a negative determination at block 220, the method 200 proceeds to block 210, where a determination is again made as to whether the threshold number of iterations for the onsite testing has been reached. If not (a negative determination at block 210), then the onsite testing is again initiated at block 212. If, however, the threshold number of iterations for the onsite testing is reached—indicating that there is still significant uncertainty as to whether the player has suffered a potential neurological injury after several iterations of the onsite testing—then a medical evaluation of the player may be initiated at block 224 of the method 200. In example embodiments, the interrupt 124 may be issued prior to initiating the medical evaluation at block 224. Further, in example embodiments, the medical evaluation may be the more comprehensive concussion protocol testing described earlier, which may be performed on the sideline or at another onsite or offsite location and may involve machine-based testing such as magnetic resonance imaging (MRI) testing, computed tomography (CT) testing, X-ray testing, or the like.

Different iterations of the onsite testing may involve different request/response data 122. For instance, questions/requests presented to the player during a given iteration of the onsite testing may be modified, eliminated, replaced, supplemented, or the like for a subsequent iteration of the onsite testing if the player's responses to such questions/requests result in ambiguity as to whether the player has suffered a neurological injury. As a non-limiting example, if a player's voice response to the question "are you OK?" is unclear from the audio data that is captured or if the number of fingers the player raises in response to a request to raise X number of fingers is unclear from the video data, these questions/requests may be modified or supplemented in subsequent iteration of the onsite testing in order to obtain less ambiguous responses from the player. As another non-limiting example, if inertial sensor data indicative of the player's movements during a given iteration of onsite testing is ambiguous as to whether the player's movements substantially deviate from expected movements for the player, sensor data indicative of the player's movements may be captured over a longer period of time or in response to different triggers during a subsequent iteration of the onsite testing.

In example embodiments, the threshold values to which the updated likelihood of neurological injury is compared at blocks 218 and 220 as well as the threshold risk level used to determine whether to initiate the onsite testing may be different for different players based on their baseline risk profiles. For instance, a player who is more susceptible to neurological injury based on her baseline risk profile may be associated with a lower first threshold value at block 218; a higher second threshold value at block 220; and/or a lower threshold risk level. Conversely, a player who is less susceptible to neurological injury based on his baseline risk profile may be associated with a higher first threshold value at block 218; a lower second threshold value at block 220; and/or a higher threshold risk level. In this manner, for similar sensor data 112 and similar request/response data 122, onsite testing and/or the more comprehensive evaluation subsequent to the onsite testing may be more likely to be triggered for a player is more susceptible to neurological injury as compared to a player who is less susceptible to neurological injury. The threshold risk level and/or the threshold values for a given player may be based on any type of information contained in the corresponding baseline risk profile including, without limitation, his historical on-field interactions; the position he plays; his physical attributes (e.g., weight, height, age, etc.); the number of prior neurological injuries and the extent of injury; the risk of neurological injury presented to the player by opponents; and so forth.

In example embodiments, in response to the cognitive analysis performed at block 206 by the cognitive engine 110 that reveals at least a threshold risk of neurological injury to a player, the onsite testing engine 120 communicates with onsite devices to conduct an onsite test (e.g., a concussion protocol field test) through the exchange of request/response data 122 between the onsite testing engine 120 and the onsite devices. The onsite testing can be performed in dynamically in real-time such that a high risk of neurological injury can be identified at an early stage and the player removed from the playing field before potentially more serious long-term consequences result. In example embodiments, the request/response protocol for the onsite testing may include presenting a request to the player to perform an action (e.g., "raise your hand," "put up three fingers," etc.) and capturing sensor data (e.g., video data) indicative of the player performing, attempting to perform, or failing to perform the action. Further, in example embodiments, the request/response protocol for the onsite testing may include asking the player a set of questions that she is expected to immediately know the answer to such as "who is the current President of the United States?" or "when is your birthday." A delayed response from the player may be indicative of potential neurological injury.

In addition, in example embodiments, the request/response protocol for the onsite testing may include questions/requests designed to test the player's range of physical movement. For instance, the player's eye movement may be tracked by asking the player to follow with her eyes the changing position of a light. The light may be, for example, emitted from a projection element integrated in the player's helmet. As another non-limiting example, the player may be asked to perform a specific action or a specific series of actions. The player's response can then be evaluated as part of the cognitive analysis performed at block 216 to determine how accurately the player performed the actions. For instance, a player can be asked to walk in a straight line for some period of time; raise his head for some period of time; raise one leg followed by the other leg; or any other one or more physical movements. Video data, inertial sensor data, or the like can be captured of the player's response to such requests and provided as part of the request/response data to the cognitive engine 110 for cognitive analysis.

Figure 3:
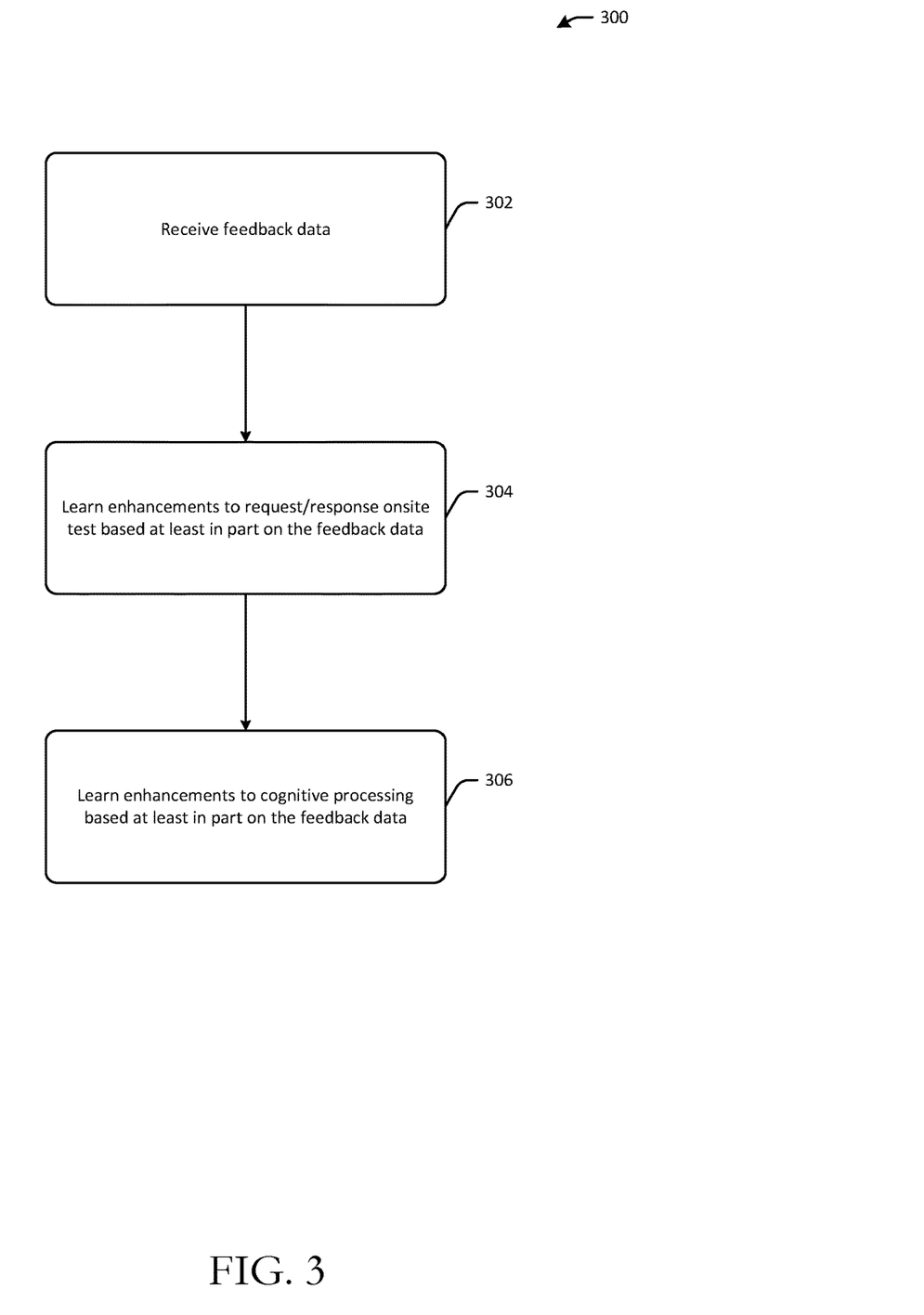
FIG. 3 is a process flow diagram of an illustrative method for learning enhancements to smart prediction of neurological injury in accordance with one or more example embodiments.

FIG. 3 is a process flow diagram of an illustrative method 300 for learning enhancements to smart prediction of neurological injury in accordance with one or more example embodiments. FIG. 3 will be described in conjunction with FIG. 1 hereinafter. At block 302 of the method 300, the cognitive engine 110 may receive feedback data 126. The feedback data 126 may include, for example, output data corresponding to prior cognitive analyses performed by the cognitive engine 110. For instance, the feedback data 126 may include data associated with a scenario in which a player suffered a neurological injury and the cognitive analysis revealed a high likelihood of neurological injury; data associated with a scenario in which a player suffered a neurological injury but the cognitive analysis revealed a low or ambiguous likelihood of neurological injury; data associated with a scenario in which a player did not suffer a neurological injury and the cognitive analysis revealed a low likelihood of neurological injury; and/or data associated with a scenario in which a player did not suffer a neurological injury but the cognitive analysis revealed a high likelihood of neurological injury. Thus, the feedback data 126 may include sensor data 112 and/or request/response data 122 corresponding to "false positive" and "false negative" scenarios as well as scenarios in which the cognitive analyses accurately predicted the presence or absence of neurological injury.

Then, at block 304 of the method 300, the cognitive engine 110 may learn enhancements to the request/response onsite testing based at least in part on the feedback data 126. For instance, the cognitive engine 110 may eliminate or modify certain questions/requests in the onsite testing that tend to result in false negative or false positive scenarios. Similarly, at block 306 of the method 300, the cognitive engine 110 may learn enhancements to the cognitive analysis performed at block 206 of the method 200 and/or the cognitive analysis performed at block 216 of the method 200 based at least in part on the feedback data 126. For instance, the cognitive engine 110 may utilize the feedback data 126 to refine the baseline risk profile for a player and/or to refine the threshold values used as part of the cognitive processing to determine the player's likelihood of neurological injury for a given set of sensor data 112. Further, in example embodiments, as the cognitive engine 110 learns more scenarios that are more likely to result in an accurate prediction of neurological injury, a sports governing body can use this information to enact rules or regulations to mitigate the risk of neurological injury in such scenarios.

One or more illustrative embodiments of the disclosure are described herein. Such embodiments are merely illustrative of the scope of this disclosure and are not intended to be limiting in any way. Accordingly, variations, modifications, and equivalents of embodiments disclosed herein are also within the scope of this disclosure.

Figure 4:
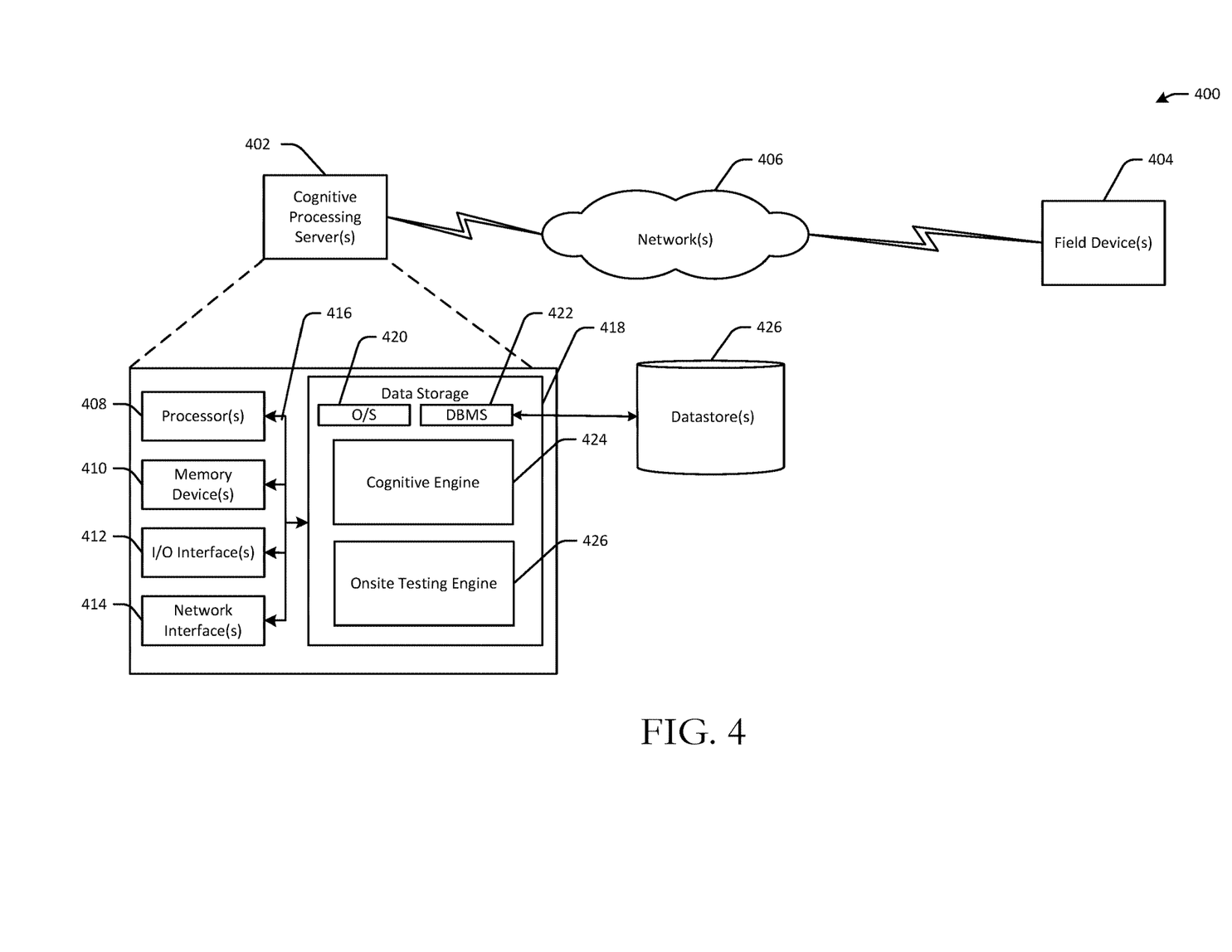
FIG. 4 is a schematic diagram of an illustrative networked architecture configured to implement one or more example embodiments.

FIG. 4 is a schematic diagram of an illustrative networked architecture 400 configured to implement one or more example embodiments of the disclosure. The illustrative networked architecture 400 includes one or more cognitive processing servers 402 configured to communicate via one or more networks 406 with one or more field devices 404. The field device(s) 404 may include devices that are used in connection with an activity involving physical contact such as an athletic contest. The field device(s) 404 may include, without limitation, a personal computer (PC), a tablet, a smartphone, a wearable device, a voice-enabled device, or the like. The field device(s) 404 may further include one or more sensors disposed in an environment in which the activity is taking place or integrated, affixed, or otherwise associated with equipment, uniforms, or the like worn by participants in the activity. Such sensors may capture the sensor data 112 evaluated by the cognitive engine 110 (FIG. 1). Such sensors may include, without limitation, an inertial sensor (e.g., an accelerometer, a gyroscope, etc.); a vibration sensor; a force sensor; an image sensor; a sensor that takes biophysical measurements (e.g., a blood pressure sensor, a heart rate sensor; an electrocardiography (EKG) sensor or the like that measures electrical activity of the heart; a sensor to measure brain activity; and so forth. In certain example embodiments, any of the example sensors identified above can be integrated with another field device 404. While any particular component of the networked architecture 400 may be described herein in the singular, it should be appreciated that multiple instances of any such component may be provided, and functionality described in connection with a particular component may be distributed across multiple ones of such a component.

The network(s) 406 may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. The network(s) 406 may have any suitable communication range associated therewith and may include, for example, global networks (e.g., the Internet), metropolitan area networks (MANs), wide area networks (WANs), local area networks (LANs), or personal area networks (PANs). In addition, the network(s) 406 may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In an illustrative configuration, the cognitive processing server 402 may include one or more processors (processor(s)) 408, one or more memory devices 410 (generically referred to herein as memory 410), one or more input/output ("I/O") interface(s) 412, one or more network interfaces 414, and data storage 418. The cognitive processing server 402 may further include one or more buses 416 that functionally couple various components of the cognitive processing server 402.

The bus(es) 416 may include at least one of a system bus, a memory bus, an address bus, or a message bus, and may permit the exchange of information (e.g., data (including computer-executable code), signaling, etc.) between various components of the cognitive processing server 402. The bus(es) 416 may include, without limitation, a memory bus or a memory controller, a peripheral bus, an accelerated graphics port, and so forth. The bus(es) 416 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 410 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 410 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 410 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 418 may include removable storage and/or non-removable storage including, but not limited to, magnetic storage, optical disk storage, and/or tape storage. The data storage 418 may provide non-volatile storage of computer-executable instructions and other data. The memory 410 and the data storage 418, removable and/or non-removable, are examples of computer-readable storage media (CRSM) as that term is used herein.

The data storage 418 may store computer-executable code, instructions, or the like that may be loadable into the memory 410 and executable by the processor(s) 408 to cause the processor(s) 408 to perform or initiate various operations. The data storage 418 may additionally store data that may be copied to memory 410 for use by the processor(s) 408 during the execution of the computer-executable instructions. Moreover, output data generated as a result of execution of the computer-executable instructions by the processor(s) 408 may be stored initially in memory 410 and may ultimately be copied to data storage 418 for non-volatile storage.

More specifically, the data storage 418 may store one or more operating systems (O/S) 420; one or more database management systems (DBMS) 422 configured to access the memory 410 and/or one or more external datastores 426; and one or more program modules, applications, engines, managers, computer-executable code, scripts, or the like such as, for example, a cognitive engine 424 and an onsite testing engine 426. Any of the components depicted as being stored in data storage 418 may include any combination of software, firmware, and/or hardware. The software and/or firmware may include computer-executable instructions (e.g., computer-executable program code) that may be loaded into the memory 410 for execution by one or more of the processor(s) 408 to perform any of the operations described earlier in connection with correspondingly named modules/engines.

Although not depicted in FIG. 4, the data storage 418 may further store various types of data utilized by components of the cognitive processing server 402 (e.g., data stored in the datastore(s) 426). Any data stored in the data storage 418 may be loaded into the memory 410 for use by the processor(s) 408 in executing computer-executable instructions. In addition, any data stored in the data storage 418 may potentially be stored in the external datastore(s) 426 and may be accessed via the DBMS 422 and loaded in the memory 410 for use by the processor(s) 408 in executing computer-executable instructions.

The processor(s) 408 may be configured to access the memory 410 and execute computer-executable instructions loaded therein. For example, the processor(s) 408 may be configured to execute computer-executable instructions of the various program modules, applications, engines, managers, or the like of the cognitive processing server 402 to cause or facilitate various operations to be performed in accordance with one or more embodiments of the disclosure. The processor(s) 408 may include any suitable processing unit capable of accepting data as input, processing the input data in accordance with stored computer-executable instructions, and generating output data. The processor(s) 408 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 408 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 408 may be capable of supporting any of a variety of instruction sets.

Referring now to other illustrative components depicted as being stored in the data storage 418, the O/S 420 may be loaded from the data storage 418 into the memory 410 and may provide an interface between other application software executing on the cognitive processing server 402 and hardware resources of the cognitive processing server 402. More specifically, the O/S 420 may include a set of computer-executable instructions for managing hardware resources of the cognitive processing server 402 and for providing common services to other application programs. In certain example embodiments, the O/S 420 may include or otherwise control the execution of one or more of the program modules, engines, managers, or the like depicted as being stored in the data storage 418. The O/S 420 may include any operating system now known or which may be developed in the future including, but not limited to, any server operating system, any mainframe operating system, or any other proprietary or non-proprietary operating system.

The DBMS 422 may be loaded into the memory 410 and may support functionality for accessing, retrieving, storing, and/or manipulating data stored in the memory 410, data stored in the data storage 418, and/or data stored in external datastore(s) 426. The DBMS 422 may use any of a variety of database models (e.g., relational model, object model, etc.) and may support any of a variety of query languages. The DBMS 422 may access data represented in one or more data schemas and stored in any suitable data repository. Data stored in the datastore(s) 426 may include, for example, baseline risk profiles; sensor data; cognitive analysis data; etc. External datastore(s) 426 that may be accessible by the cognitive processing server 402 via the DBMS 422 may include, but are not limited to, databases (e.g., relational, object-oriented, etc.), file systems, flat files, distributed datastores in which data is stored on more than one node of a computer network, peer-to-peer network datastores, or the like.

Referring now to other illustrative components of the cognitive processing server 402, the input/output (I/O) interface(s) 412 may facilitate the receipt of input information by the cognitive processing server 402 from one or more I/O devices as well as the output of information from the cognitive processing server 402 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the cognitive processing server 402 or may be separate. The I/O devices may further include, for example, any number of peripheral devices such as data storage devices, printing devices, and so forth.

The I/O interface(s) 412 may also include an interface for an external peripheral device connection such as universal serial bus (USB), FireWire, Thunderbolt, Ethernet port or other connection protocol that may connect to one or more networks. The I/O interface(s) 412 may also include a connection to one or more antennas to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, WiMAX network, 3G network, etc.

The cognitive processing server 402 may further include one or more network interfaces 414 via which the cognitive processing server 402 may communicate with any of a variety of other systems, platforms, networks, devices, and so forth. The network interface(s) 414 may enable communication, for example, with one or more other devices via one or more of the network(s) 406.

It should be appreciated that the program modules/engines depicted in FIG. 4 as being stored in the data storage 418 are merely illustrative and not exhaustive and that processing described as being supported by any particular module may alternatively be distributed across multiple modules, engines, or the like, or performed by a different module, engine, or the like. In addition, various program module(s), script(s), plug-in(s), Application Programming Interface(s) (API(s)), or any other suitable computer-executable code hosted locally on the cognitive processing server 402 and/or other computing devices accessible via one or more networks, may be provided to support functionality provided by the modules depicted in FIG. 4 and/or additional or alternate functionality. Further, functionality may be modularized in any suitable manner such that processing described as being performed by a particular module may be performed by a collection of any number of program modules, or functionality described as being supported by any particular module may be supported, at least in part, by another module. In addition, program modules that support the functionality described herein may be executable across any number of cluster members in accordance with any suitable computing model such as, for example, a client-server model, a peer-to-peer model, and so forth. In addition, any of the functionality described as being supported by any of the modules depicted in FIG. 4 may be implemented, at least partially, in hardware and/or firmware across any number of devices.

It should further be appreciated that the cognitive processing server 402 may include alternate and/or additional hardware, software, or firmware components beyond those described or depicted without departing from the scope of the disclosure. More particularly, it should be appreciated that software, firmware, or hardware components depicted as forming part of the cognitive processing server 402 are merely illustrative and that some components may not be present or additional components may be provided in various embodiments. While various illustrative modules have been depicted and described as software modules stored in data storage 418, it should be appreciated that functionality described as being supported by the modules may be enabled by any combination of hardware, software, and/or firmware. It should further be appreciated that each of the above-mentioned modules may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other modules. Further, one or more depicted modules may not be present in certain embodiments, while in other embodiments, additional program modules and/or engines not depicted may be present and may support at least a portion of the described functionality and/or additional functionality.

One or more operations the method 200 and/or the method 300 may be performed by one or more cognitive processing servers 402 having the illustrative configuration depicted in FIG. 4, or more specifically, by one or more program modules, engines, applications, or the like executable on such a device. It should be appreciated, however, that such operations may be implemented in connection with numerous other device configurations.

The operations described and depicted in the illustrative methods of FIGS. 2A, 2B, and 3 may be carried out or performed in any suitable order as desired in various example embodiments of the disclosure. Additionally, in certain example embodiments, at least a portion of the operations may be carried out in parallel. Furthermore, in certain example embodiments, less, more, or different operations than those depicted in FIGS. 2A, 2B, and 3 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular system, system component, device, or device component may be performed by any other system, device, or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure. In addition, it should be appreciated that any operation, element, component, data, or the like described herein as being based on another operation, element, component, data, or the like may be additionally based on one or more other operations, elements, components, data, or the like. Accordingly, the phrase "based on," or variants thereof, should be interpreted as "based at least in part on."

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for predicting a neurological injury to a particular participant in an activity, the method comprising:
   receiving sensor data relating to interactions between a plurality of participants in the activity, the plurality of participants including the particular participant;
   determining a baseline neurological injury risk profile for the particular participant;
   performing, based at least in part on the sensor data and the baseline neurological injury risk profile, a cognitive risk analysis to determine a likelihood of the neurological injury to the particular participant;
   determining that the likelihood of the neurological injury to the particular participant is at least as large as a threshold risk level;
   initiating an onsite test for the neurological injury to the particular participant.

2. The computer-implemented method of claim 1, wherein the cognitive risk analysis is a first cognitive risk analysis, the method further comprising:
   receiving response data associated with administering the onsite test; and
   performing, based at least in part on the response data, a second cognitive analysis to determine an updated likelihood of the neurological injury to the particular participant.

3. The computer-implemented method of claim 2, further comprising:
   determining that the updated likelihood of the neurological injury to the particular participant is at least as large as a threshold value; and
   initiating an interrupt to the activity.

4. The computer-implemented method of claim 2, further comprising:
   determining that the updated likelihood of the neurological injury to the particular participant is not larger than a threshold value; and
   sending a notification to an onsite device that no follow-up action is needed.

5. The computer-implemented method of claim 2, wherein the response data is first response data and the updated likelihood of the neurological injury to the particular participant is a first updated likelihood, the method further comprising:
   determining that the first updated likelihood of the neurological injury to the particular participant is between a first threshold value and a second threshold value;
   initiating an additional iteration of the onsite test for the neurological injury;
   receiving second response data associated with the additional iteration of the onsite test;
   performing, based at least in part on the second response data, a third cognitive analysis to determine a second updated likelihood of the neurological injury to the particular participant;
   determining that the second updated likelihood of the neurological injury to the particular participant is between the first threshold value and the second threshold value;
   determining that a threshold number of iterations of the onsite test has been reached; and initiating a follow-up medical evaluation of the particular participant.

6. The computer-implemented method of claim 5, further comprising updating the onsite test based at least in part on the first response data prior to administering the additional iteration of the onsite test.

7. The computer-implemented method of claim 1, wherein the baseline neurological injury risk profile for the particular participant is based at least in part on at least one of: a historical risk of the neurological injury to the particular participant, a role of the particular participant in the activity, or characteristics of the activity.

8. A system for predicting a neurological injury to a particular participant in an activity, the system comprising:
at least one memory storing computer-executable instructions; and
at least one processor, wherein the at least one processor is configured to access the at least one memory and execute the computer-executable instructions to:
receive sensor data relating to interactions between a plurality of participants in the activity, the plurality of participants including the particular participant;
determine a baseline neurological injury risk profile for the particular participant;
perform, based at least in part on the sensor data and the baseline neurological injury risk profile, a cognitive risk analysis to determine a likelihood of the neurological injury to the particular participant;
determine that the likelihood of the neurological injury to the particular participant is at least as large as a threshold risk level;
initiate an onsite test for the neurological injury to the particular participant.

9. The system of claim 8, wherein the cognitive risk analysis is a first cognitive risk analysis, and wherein the at least one processor is further configured to execute the computer-executable instructions to:
receive response data associated with administering the onsite test; and
perform, based at least in part on the response data, a second cognitive analysis to determine an updated likelihood of the neurological injury to the particular participant.

10. The system of claim 9, wherein the at least one processor is further configured to execute the computer-executable instructions to:
determine that the updated likelihood of the neurological injury to the particular participant is at least as large as a threshold value; and
initiate an interrupt to the activity.

11. The system of claim 9, wherein the at least one processor is further configured to execute the computer-executable instructions to:
determine that the updated likelihood of the neurological injury to the particular participant is not larger than a threshold value; and
send a notification to an onsite device that no follow-up action is needed.

12. The system of claim 9, wherein the response data is first response data and the updated likelihood of the neurological injury to the particular participant is a first updated likelihood, and wherein the at least one processor is further configured to execute the computer-executable instructions to:
determine that the first updated likelihood of the neurological injury to the particular participant is between a first threshold value and a second threshold value;
initiate an additional iteration of the onsite test for the neurological injury;
receive second response data associated with the additional iteration of the onsite test;
perform, based at least in part on the second response data, a third cognitive analysis to determine a second updated likelihood of the neurological injury to the particular participant;
determine that the second updated likelihood of the neurological injury to the particular participant is between the first threshold value and the second threshold value;
determine that a threshold number of iterations of the onsite test has been reached; and
initiate a follow-up medical evaluation of the particular participant.

13. The system of claim 12, wherein the at least one processor is further configured to execute the computer-executable instructions to update the onsite test based at least in part on the first response data prior to administering the additional iteration of the onsite test.

14. The system of claim 8, wherein the baseline neurological injury risk profile for the particular participant is based at least in part on at least one of: a historical risk of the neurological injury to the particular participant, a role of the particular participant in the activity, or characteristics of the activity.

15. A computer program product for predicting a neurological injury to a particular participant in an activity, the computer program product comprising a storage medium readable by a processing circuit, the storage medium storing instructions executable by the processing circuit to cause a method to be performed, the method comprising:
receiving sensor data relating to interactions between a plurality of participants in the activity, the plurality of participants including the particular participant;
determining a baseline neurological injury risk profile for the particular participant;
performing, based at least in part on the sensor data and the baseline neurological injury risk profile, a cognitive risk analysis to determine a likelihood of the neurological injury to the particular participant;
determining that the likelihood of the neurological injury to the particular participant is at least as large as a threshold risk level;
initiating an onsite test for the neurological injury to the particular participant.

16. The computer program product of claim 15, wherein the cognitive risk analysis is a first cognitive risk analysis, the method further comprising:
receiving response data associated with administering the onsite test; and
performing, based at least in part on the response data, a second cognitive analysis to determine an updated likelihood of the neurological injury to the particular participant.

17. The computer program product of claim 16, the method further comprising:
determining that the updated likelihood of the neurological injury to the particular participant is at least as large as a threshold value; and
initiating an interrupt to the activity.

18. The computer program product of claim 16, the method further comprising:
determining that the updated likelihood of the neurological injury to the particular participant is not larger than a threshold value; and sending a notification to an onsite device that no follow-up action is needed.

19. The computer program product of claim 16, wherein the response data is first response data and the updated likelihood of the neurological injury to the particular participant is a first updated likelihood, the method further comprising:
 determining that the first updated likelihood of the neurological injury to the particular participant is between a first threshold value and a second threshold value;
 initiating an additional iteration of the onsite test for the neurological injury;
 receiving second response data associated with the additional iteration of the onsite test;
 performing, based at least in part on the second response data, a third cognitive analysis to determine a second updated likelihood of the neurological injury to the particular participant;
 determining that the second updated likelihood of the neurological injury to the particular participant is between the first threshold value and the second threshold value;
 determining that a threshold number of iterations of the onsite test has been reached; and
 initiating a follow-up medical evaluation of the particular participant.

20. The computer program product of claim 19, the method further comprising updating the onsite test based at least in part on the first response data prior to administering the additional iteration of the onsite test.

* * * * *